United States Patent
Backes et al.

(10) Patent No.: US 11,485,930 B2
(45) Date of Patent: Nov. 1, 2022

(54) METHOD FOR PRODUCING AN AROMA MIXTURE CONTAINING UNSATURATED DIENALS

(71) Applicant: SYMRISE AG, Holzminden (DE)

(72) Inventors: Michael Backes, Holzminden (DE); Jekaterina Ongouta, Stadtoldendorf (DE); Jakob Ley, Holzminden (DE); Tobias Vössing, Beverungen (DE); Volkmar Koppe, Höxter-Stahle (DE); Jens Koch, Eschershausen (DE)

(73) Assignee: SYMRISE AG, Holzminden (DE)

( * ) Notice: Subject to any disclaimer, the term of this patent is extended or adjusted under 35 U.S.C. 154(b) by 188 days.

(21) Appl. No.: 16/615,863

(22) PCT Filed: Jun. 1, 2017

(86) PCT No.: PCT/EP2017/063368
§ 371 (c)(1),
(2) Date: Nov. 22, 2019

(87) PCT Pub. No.: WO2018/219467
PCT Pub. Date: Dec. 6, 2018

(65) Prior Publication Data
US 2020/0080023 A1    Mar. 12, 2020

(51) Int. Cl.
*C11B 9/00* (2006.01)
*A23L 27/20* (2016.01)
*A23L 27/00* (2016.01)
*A23L 27/26* (2016.01)
*A23L 27/29* (2016.01)
*A23L 23/10* (2016.01)

(52) U.S. Cl.
CPC .......... *C11B 9/0015* (2013.01); *A23L 23/10* (2016.08); *A23L 27/2024* (2016.08); *A23L 27/26* (2016.08); *A23L 27/29* (2016.08); *A23L 27/88* (2016.08); *A23V 2002/00* (2013.01)

(58) Field of Classification Search
CPC .... C11B 9/0015; A23L 27/2024; A23L 27/88; A23L 27/26; A23L 27/29; A23L 23/10; A23V 2002/00
USPC ........................................................ 426/534
See application file for complete search history.

(56) References Cited

U.S. PATENT DOCUMENTS

2004/0214299 A1*  10/2004  Kerler ................... A23L 27/24
435/147

FOREIGN PATENT DOCUMENTS

| EP | 0911414 A1 | 4/1999 |
|---|---|---|
| EP | 1244364 A1 | 10/2002 |
| EP | 1336659 A2 | 8/2003 |
| WO | 02103023 A2 | 12/2002 |

OTHER PUBLICATIONS

International Search Report and Written Opinion dated Mar. 29, 2018 for corresponding PCT Application No. PCT/EP2017/063368.

* cited by examiner

*Primary Examiner* — Brent T O'Hern
(74) *Attorney, Agent, or Firm* — Polsinelli PC

(57) ABSTRACT

The present invention primarily relates to a method for producing an aromatic blend comprising unsaturated dienals. The invention further relates to aromatic blends obtained or obtainable by a method according to the invention and compositions or semi-finished products for producing said compositions, comprising aromatic blends according to the invention. A further aspect of the present invention relates to the use of an aromatic blend according to the invention for aromatizing a composition, preferably a composition serving for food or pleasure, or a semi-finished product for producing such a composition.

14 Claims, No Drawings

METHOD FOR PRODUCING AN AROMA MIXTURE CONTAINING UNSATURATED DIENALS

CROSS-REFERENCE TO RELATED APPLICATIONS

This application is a national stage application (under 35 U.S.C. § 371) of PCT/EP2017/063368, filed Jun. 1, 2017, which is incorporated herein by reference in its entirety.

The present invention primarily relates to a method for producing an aromatic blend comprising unsaturated dienals. The invention further relates to aromatic blends obtained or obtainable by a method according to the invention and compositions or semi-finished products for producing said compositions, comprising aromatic blends according to the invention. A further aspect of the invention relates to the use of an aromatic blend according to the invention for aromatization of a composition, preferable a composition serving for nutrition or pleasure or of a semi-finished product for producing such a composition.

Further aspects and preferred embodiments of the present invention result from the following explanations, the attached examples and particularly the attached claims.

The targeted production and use of aromatic blends of certain flavours, which are compatible to food law, is a subject of constant research efforts.

The flavourings which are particularly interesting for the aroma industry include the e.g. polyunsaturated aldehydes, particularly 2E,4E-decadienal and 2E,4E-nonadienal as well as their mixtures with their respective stereoisomeric forms ((2Z,4E), (2E,4Z) and (2Z,4Z)). 2,4-nonadienal (FEMA 3212, EFSA 05.071 and 05.194) and 2,4-decadienal (FEMA 3135; EFSA 05.081 and 05.140) themselves are known aromatic substances which are applied to many aromatic blends.

Mixtures comprising 2,3-nonadienal or 2,4-decadienal are characteristic for a particularly authentic meat taste (particularly chicken and beef) in many applications, but are also used in fruit and vegetable aromas (e.g. pear, asparagus or, respectively, tomato aroma) as well as for aromatizing of spirits (e.g. of whiskey, tequila, brandy).

The production of aromatic substances comprising polyunsaturated aldehydes is usually performed fully-synthetically from smaller components via coupling reactions or by concentration of bypass flows of the refining of edible oils. In these oils, saturated and unsaturated aldehydes are formed in traces by (partially enzymatic) reactions in connection with air and are often responsible for a rancid undesired aroma and are thus preferably removed.

However, these aldehydes are valuable raw materials for aroma compositions, which are not always available or only for a very high price.

The primary object was thus to find new, preferably cost-effective and simple, production methods for providing aromatic blends comprising unsaturated dienals.

This primary object is solved according to the invention by a method for producing an aromatic blend comprising one or more unsaturated dienal(s), comprising or consisting of the steps a) air oxidation of one or more educt(s) comprising or consisting of one or more substance(s) selected from the group consisting of punicic acid, punicic acid ester, elaeostearinic acid, elaeostearinic acid ester, linoleic acid and linoleic acid ester, b) optionally disintegration of a part or all or substantially all peroxides in the mixture obtained in step a), c) purification or, respectively, concentration of the dienal(s) produced in step a) of the mixture obtained in step a) and/or b), if present.

Punicic acid and/or a punicic acid ester and/or elaeostearinic acid and/or an elaeostearinic acid ester are used as educt(s) in step a) for producing an aromatic blend comprising 2,4-nonadienal according to a preferred embodiment of the method according to the invention.

Linoleic acid and/or a linoleic acid ester are used as educt(s) in step a) for producing an aromatic blend comprising 2,4-decadienal according to another preferred embodiment of the method according to the invention.

In the scope of the present text, the term "2,4-nonadienal" represents a single stereoisomer of this compound, i.e. (2E,4E), (2Z,4E), (2E,4Z) or (2Z,4Z)-nonadienal, or represents a mixture of two or more of these stereoisomeric forms. The same applies analogously for 2,4-decadienal.

Surprisingly it was found that the method according to the invention enables particularly the production of 2,4-nonadienal as well as 2,4-decadienal in a sensorically acceptable, in many cases even preferred quality compared to the prior art.

With the aid of the method according to the invention, the following advantages can advantageously be obtained or, respectively observed:

The method is applicable without concerns regarding food technology and food law.

The method may be repeated several times to increase the yield.

The method does not require uncommon steps or procedures so that it may be easily performed with usual production facilities.

The method yields a product with a complex aroma profile which is described as particularly authentic.

The method is based on the use of renewable raw materials and without the use of stoichiometric reagents or metallic catalysts.

The method enables an easy and cost-effective application.

The term "punicic acid" is meant to be understood in the scope of the present text to be pure punicic acid ((9Z,11E,13Z)-octadeca-9,11,13-trienic acid).

The term "punicic acid ester" is meant to be understood in the scope of the present text as the esters of the punicic acid, preferably the methyl, ethyl or hydroxyl alkyl ester thereof. Particularly preferred are glycerol monoester, glycerol diester and glycerol trimester of the punicic acid and their mixtures.

The term "elaeostearinic acid" is meant to be understood in the scope of the present text as pure alpha-elaeostearinic acid ((9Z,11E,13E)-Octadeca-9,11,13-trienic acid) or, respectively pure beta-elaeostearinic acid ((9E,11E,13E)-Octadeca-9,11,13-trienic acid) as well as their mixtures.

The term "elaeostearinic acid ester" is meant to be understood in the scope of the present text as the esters of the alpha-elaeostearinic acid or, respectively, of the beta-elaeostearinic acid, preferably the methyl, ethyl or hydroxyl alkyl ester as well as their mixtures. Particularly preferred are glycerol monoester, glycerol diester and glycerol trimester of the elaeostearinic acid and their mixtures.

The term "linoleic acid" is meant to be understood as pure linoleic acid ((9Z,12Z)-Octadeca-9,12-dienic acid).

The term "linoleic acid ester" is meant to be understood as the esters of the linoleic acid, preferably the methyl, ethyl or hydroxyl alkyl ester. Particularly preferred are glycerol monoester, glycerol diester and glycerol trimester of the linoleic acid and their mixtures.

In the scope of the method according to the invention, educts which contain punicic acid (ester), elaeostearinic acid (ester) and/or linoleic acid (ester) or, respectively, mixtures thereof, can also be used in step a) according to a preferred embodiment. Particularly preferred is the use of an oil as educt which has punicic acid, elaeostearinic acid and/or linoleic acid as substantial component of the contained glyceridically bound fatty acids. Preferred are edible oils which contain 20 to 80 wt.-% of bound punicic acid, elaeostearinic acid and/or linoleic acid.

In case of oils containing punicic acid or, respectively, elaeostearinic acid, pomegranate seed oil, snake cucumber seed oil, bitter melon seed oil as well as tung oil are particularly suitable for use as educts in step a) of the method according to the invention. Preferred is the use of pomegranate seed oil.

In case of oils containing linoleic acid, grape seed oil, thistle oil, hempseed oil, soy oil, wheat germ oil, corn seed oil as well as sunflower oil are particularly suitable for use as educts in step a) of the method according to the invention. Preferred is the use of sunflower oil with a proportion of linoleic acid as high as possible, particularly preferably with a proportion of linoleic acid of 40 wt.-%.

According to a further preferred embodiment of the method according to the invention, when an oil with a proportion of glyceridically bound punicic acid, elaeostearinic acid and/or linoleic acid or with a proportion of other esters of the punicic acid, the elaeostearinic acid and/or linoleic acid, the free unsaturated fatty acid, preferably with a proportion in the range of from 5 to 10 wt.-%, related to the total amount of educt(s) is added as educt before step a) in addition to the punicic acid, elaeostearinic acid and/or linoleic acid bound in the oil. Particularly preferably re in this case free punicic acid, elaeostearinic acid and/or linoleic acid are added.

Preferred is a method according to the invention as described above, wherein after purification or, respectively, concentration in step c) a residue is obtained which contains a residual amount of educt(s) and wherein the method additionally comprises the following step:

d) repeating, preferably multiple repeating, of the previously defined steps, wherein the residue obtained at the purification or, respectively, concentration in step c) is used in step a).

Preferably, the sequence of the described steps of the method according to the invention is in total repeated three to five times, preferably four times.

The (particularly multiple) return of the residue obtained at the purification or, respectively, concentration in step c) of the method, i.e. the return of the educts in the mixture, which have not yet been reacted to unsaturated dienals in the first reaction cycle, into the method is particularly suitable as then the yield of the method can be significantly enhanced and the scrap material can be minimized. This in turn leads to high cost savings by applying the method according to the invention.

According to a further preferred embodiment of the method according to the invention, step a) is performed in the presence of one or further solvent(s), preferably wherein the, one or two solvent(s) is/are triacetin and/or triethyl citrate, particularly preferably wherein in total 2 to 20 wt.-%, further preferably 5 to 15 wt.-%, each related to the total weight of the educt(s), of solvent(s), preferably triacetin and/or triethyl citrate, are used.

According to a further preferred embodiment of the method according to the invention, an amount of air of 10 to 1000 l/h, preferably 30 to 500 l/h, particularly preferably 40 to 100 l/h per kg educt(s) is used for the air oxidation in step a).

Preferably, the air oxidation is performed by treatment by gas with (ambient) air. The use of an amount of air of from 10 to 1000 l/h per kg educt(s) has been found to be particularly advantageous. In case of lower amounts of air, usually the yield is too low, higher amounts of air often lead to the formation of side-products or degradation of the resulting desired products.

According to a further preferred embodiment of the method according to the invention, the air oxidation in step a) is performed at a temperature of from 30 to 200° C., preferably of from 70 to 200° C., preferably of from 80 to 200° C., preferably of from 90 to 170° C., further preferably of from 100 to 130° C.

Preferably, the air oxidation in step a) of the method according to the invention is performed over a time of from 1 to 30 h, preferably 2 to 12 h, particularly preferably of from 4 to 12 h.

The application of the air oxidation in step a) of the method according to the invention over a time of from 1 to 30 h is particularly advantageous as longer times of reaction often lead to the formation of undesired side-products in too high amounts.

According to a preferred embodiment of the method according to the invention, step a) is performed at a temperature of from 10 to 130° C. and/or within a time of from 2 to 12 h.

According to a further alternative embodiment of the method according to the invention, step a) is performed at a temperature of from 30 to 70° C. and/or within a time of from 4 to 12 h.

Preferably, the degradation of a part or all or substantially all peroxides of the mixture obtained in step a) is performed in step b), if present, of the method according to the invention by heating, preferably to temperatures of from 100 to 200° C., preferably within a time of from 0.5 to 5 h.

If the mixture obtained in step a) of the method according to the invention has a peroxide number of more than 30 meg O/kg, it is advantageous to reduce the peroxide number by heating before step c) of the method to less than 30 meg O/kg, preferably less than 20 meg O/kg. The peroxide number is thus preferably determined by the Wheeler method.

The degradation of a part or all or substantially all peroxides of the mixture obtained in step a) before the purification or, respectively, concentration applied in step c) of the method according to the invention is particularly advantageous due to safety reasons. The application of step b) in the method according to the invention is further particularly advantageous as such a method leads to more stable mixtures (with regard to aromas) and to a higher amount of dienals in the aromatic blend, as the peroxides do not react over long times or, respectively, not just during the purification or, respectively, concentration in step c) of the method according to the invention, when the mixture becomes more concentrated.

According to a preferred embodiment, step b) of the method according to the invention is performed at a temperature of from 120 to 140° C. and/or within a time of from 1.5 to 2.5 h.

Alternatively and according to a further preferred embodiment, step b) of the method according to the invention is performed at a temperature of from 160 to 180° C. and/or within a time of from 0.5 to 1.5 h.

Preferably, the purification or, respectively, concentration in step c) of the method according to the invention is performed by distillation, preferably fractioned distillation.

Preferably, highly volatile compounds are first separated during the distillation. This has often proven advantageous, as such undesired wrong scents (e.g. fruity and green scents or pungent olfactory impressions) which can arise due to present small chain saturated and unsaturated aldehydes in the mixture can be removed from the aromatic blend effectively in many applications and in a simple manner.

A method according to the invention is preferred, wherein one or more solvents, preferably triacetin, is/are added before the being of the purification or, respectively, concentration in step c), preferably in a total amount of from 1 to 60 wt.-%, preferably 1 to 40 wt.-%, particularly preferably 2 to 20 wt.-%, each related to the total weight of the educt(s).

According to a preferred embodiment of the method according to the invention, a washing step with alkaline, aqueous solution (e.g. an aqueous sodium hydrogen carbonate solution) is performed before the begin of the purification or, respectively, concentration in step c), preferably before the distillation.

Such an approach is particularly advantageous as due to this additional purification, potentially present acids are removed from the mixture before the distillation.

The present invention relates in a further aspect to an aromatic blend obtained or obtainable by a method as described above.

An aromatic blend obtained or obtainable by a method as described above comprises the reaction product(s) 2,4-nonadienal and/or 2,4-decadienal as defined above. Depending on the selection of the reaction conditions, different isomer rations for 2,4-nonadienal and 2,4-decadienal are obtained.

The aromatic blends according to the invention, obtained or obtainable by a method as described above, are particularly advantageous as they have particularly complex and authentic olfactory and taste profile due to the presence of e.g. further aldehydes in addition to the smell or, respectively, taste determining 2,4-nonadienal and/or 2,4-decadienal. They may thus be particularly advantageously suitable to be used in compositions and semi-finished products according to the invention (as described below). Also, the aromatic blends according to the invention can be obtained without the addition of further chemicals (except for air oxygen) in a cost-sensitive manner and environmentally friendly from renewable sources, in contrast to unsaturated dienals obtained fully synthetically from smaller compounds via coupling reactions, and are suitable to be used in food without concerns with regard to food technology and food law.

In a preferred embodiment of the aromatic blend according to the invention, the weight ratio of 2E/4E-decadienal to 2E/4Z decadienal is 1:1 to 20:1, preferably 2:1 to 10:1, particularly preferably 4:1 to 5:1, and/or the weight ratio of 2E/4E-nonadienal to 2E/4Z nonadienal is 1:5 to 20:1, preferably 2:5 to 10:1 and/or the proportion of 2,4-decadienal, related to the total weight of the aromatic blend, is 0.001 to 5 wt.-%, preferably 0.1 to 10 wt.-%, preferably 0.1 to 7.5 wt.-%, particularly preferably 1.0 to 6 wt.-% and/or the proportion of 2,4-nonadienal, related to the total weight of the aromatic blend, is 0.001 to 7.5 wt.-%, preferably 0.01 to 5 wt.-%, particularly preferably 0.5 to 2.5 wt.-%.

According to a further aspect, the present invention relates to a composition, preferably a composition serving for food or pleasure, or a semi-finished product for producing said composition, comprising an aromatic blend as described above, preferably in an amount sufficient for imparting, modifying and/or enhancing one or several olfactory and/or gustatory scents selected from the group consisting of meat, particularly chicken, lamb or beef, fatty, rancid, nutty, sour, sweet, vegetable and fruit, preferably cucumber, melon, pear, apple, passionfruit, asparagus, tomato, and dairy, preferably sour cream, yoghurt, cheese.

In a preferred embodiment of the composition or, respectively, semi-finished product according to the invention, the proportion of the aromatic blend according to the invention, related to the total weight of the composition or, respectively, semi-finished product, is 0.0001 wt.-% (1 ppm) to 30 wt.-% (300000 ppm), preferably 0.0001 wt.-% (1 ppm) to 5 wt.-% (50000 ppm), preferably 0.001 wt.-% (10 ppm) to 0.5 wt.-% (5000 ppm), particularly preferably 0.01 wt.-% (100 ppm) to 0.5 wt.-% (5000 ppm), particularly preferably 0.05 wt.-% (500 ppm) to 0.2 wt.-% (2000 ppm).

The compositions according to the invention are preferably food and/or food supplements. The semi-finished products according to the invention are preferably semi-finished products for the production of food and/or food supplements.

According to a preferred embodiment, the aromatic blends or compositions or semi-finished products according to the invention comprise further, preferably volatile, aromatic substances.

Preferably, the aromatic blends or, respectively, compositions or, respectively, semi-finished products according to the invention comprise one or more ingredients selected from the group consisting of volatile organic acids, alcohols, thiols, disulfides, heterocyclic compounds (particularly pyridines, pyrrolines, thiazoles and thiazolines), aldehydes, ketones, esters and lactones.

Particularly preferred ingredients—wherein arbitrary ingredients may be combined with each other in any way—are:

organic acids:
acetic acid, butyric acid, 2- or, respectively, 3-methyl butyric acid, caprinic acid, capronic acid, phenylacetic acid;

alcohols:
ethanol, propylene glycol, 1,3-octenol, cis-3-hexenol, linalool, benzyl alcohol, p-cressol, 2,6-dimethylthiophenol, guajacol, eugenol;

disulfides/thiols
dimethyl sulfide, difurfuryl disulfide, methyl thiopropanal, 2-methyl-3-methyldithiofuran and bis(2-methyl-3-furyl)disulfide, methylfuranthiol, 2-(4-methyl-1,3-thiazol-5-yl)ethanol (sulfurol), methyltetrahydrofuranthiol, 3-methyl-2-buten-1-thiol, 3-thio-2-methylpentanol, 2-furfurylthiol, thiophenol, 2-methylthiophenol and 2-mercaptobutanon;

pyridines
2-acetylpyridine; pyrazines, further preferably methylpyrazine, 2,5-methylethylpyrazine, 2,3,5-trimethylpyrazine, acetylpyrazine, 2,3-diethyl-5-methylpyrazine, 2-ethyl-3,5-dimethylpyrazine and 2-Isopropyl-3-methoxypyrazine;

thiazoles/thiazolines:
2-acetylthiazol, 2-acetyl-2-thiazolin;

pyrrolines:
2-propionyl-1-pyrrolin and 2-acetyl-1-pyrrolin;

other heterocyclic compounds:
indol, skatol;

aldehydes:
acetaldehyde, trans-4,5-epoxy-(2E)-decenal, cis-4,5-epoxy-(2E)-decenal, trans-4,5-epoxy-(2E)-nonenal, cis-4,5-epoxy-(2E)-nonenal, (E,E)-2,4-undecadienal, (E,E,Z)-2,4,6-nonatrienal, (E)-2-undecenal, (Z)-2-decenal, (E)-2-decenal, (E)-2-nonenal, (Z)-2-nonenal, (E,Z)-2,6-nonadienal, 3-methylthiopropanal (Methional), vanillin and phenylacetaldehyde ketones:

3,4-dimethylcyclopentane-1,2-dione, 3-hydroxy-4,5-dimethylfuran-2(5H)-one (Sotolon), 2-aminoacetophenone, 3-hydroxy-4,5-dimethyl-2(5H)-furanone, 2,5-dimethyl-4-hydroxy-3-[2H]-furanone (Furaneol©), tetrahydrothiophen-3-one and 3-thiobutan-2-one;

esters and lactones:

methylbutanoate, ethyl-3-methylbutanoate, propyl-2-methylbutanoate, (Z)-6-dodecen-y-lactone, 4-hydroxy-2-nonenic acid lactone, δ-undecalactone, γ-nonalactone and γ-octalactone.

The aromatic blends or, respectively, compositions or, respectively, semi-finished products can also comprise further/other aromatic substances according to a preferred embodiment. The further aromatic substance(s) may e.g. also be used in the form of reaction flavours (Maillard-products), extracts or, respectively, essential oils of plants or plant parts or, respectively, fractions thereof, smoke flavours or other flavour providing compositions (e.g. protein[part] hydrolysates), grill-like flavours, plant extracts, spices, spice compositions, vegetable types and/or vegetable compositions.

Particularly, aromatic substances or their components are suited which cause a roasty, meaty (particularly chicken, fish, seafood, beef, pork, lamb, sheet, goat), vegetable (particularly tomato, onion, garlic, celery, leek, mushrooms, eggplants, seaweed), spicy (particularly black and white pepper, chili, bell pepper, cardamom, nutmeg, allspice, mustard and mustard-products), roasted, yeast-like, boiled, fatty, salty and/or pungent aromatic impression.

Compositions serving for food or pleasure in the light of the present invention are e.g. baked goods (e.g. bread, dry cookies, cake, other baked goods), sweets (e.g. chocolates, chocolate bar products, other bar products, fruit gum, hard and soft caramels, chewing gums), alcoholic or non-alcoholic drinks (e.g. cocoa, coffee, green tea, black tea, (black, green) tea drinks enriched with (green, black) tea extracts, rooibos-tea, other herbal teas, wine, drinks containing wine, beer, drinks containing beer, liqueurs, schnapps, brandies, lemonades containing fruits, isotonic drinks, refreshing-drinks, nectars, fruit and vegetable juices, fruit or vegetable juice preparations), instant drinks (e.g. instant cocoa drinks, instant tea drinks, instant coffee drinks), meat products (e.g. ham, fresh sausage or raw sausage compositions, spiced or marinated fresh or salt meat products), eggs or egg products (dry egg, protein, yolk), wheat products (e.g. breakfast cereals, muesli bars, pre-cooked finished-rice products), dairy products (e.g. full fat or fat-reduced or fat-free milk drinks, rice pudding, yoghurt, pudding, kefir, cream cheese, soft cheese, hard cheese, dry milk powder, whey, butter, buttermilk, partly or completely hydrolysed milk protein containing products), products made of soy protein or other soy bean fractions (e.g. soy milk and products made thereof, isolated or enzymatically treated soy protein containing drinks, soy flour containing drinks, soya lecithin containing compositions, fermented products such as tofu or tempe or products made thereof and mixtures with fruit compositions and facultative fragrances), fruit compositions (e.g. jams, sorbets, fruit sauces, fruit fillings), vegetable compositions (e.g. ketchup, sauces, dry vegetables, frozen vegetables, pre-cooked vegetables, boiled down vegetables), snacks (e.g. baked or fried potato chips or potato dough products, extrudates based on corn or peanut), products based on fat and oil or emulsions of the same (e.g. mayonnaise, remoulade, dressings, each full fat or fat-reduced), other finished-products and soups (e.g. dry soups, instant soups, pre cooked soups), spices, spice compositions as well as particularly seasonings, which are e.g. used in the field of snacks, sweetener compositions, sweetener tablets or sweetener sachets, other compositions for sweetening or whitening of drinks or other food.

The compositions or, respectively, semi-finished products according to the invention can also be pet food or, respectively, precursors for the production of pet food, according to a preferred embodiment.

Typical basic materials, excipients or additives for foodstuff or luxury food can be used as further components of compositions or, respectively, semi-finished products.

Further typical basic materials, excipients or additives for compositions, preferably compositions serving for food or pleasure, or, respectively, semi-finished products according to the invention, can be present in amounts of from 5 to 99.999999 wt.-%, preferably 10 to 80 wt.-%, related to the total weight of the composition or, respectively, semi-finished product. Further, the compositions or, respectively, semi-finished products can have water in an amount of up to 99.999999 wt.-%, preferably 5 to 80 wt.-%, related to the total weight of the composition or, respectively, semi-finished product.

Examples for typical basic materials, excipients or additives for compositions or, respectively, semi-finished products according to the invention are water, mixtures of fresh or processed, vegetable or animal basic or raw materials (e.g. raw, roasted, dried, fermented, smoked and/or cooked meat, bone, cartilage, fish, vegetable, fruits, herbs, nuts, vegetable or fruit juices or pastes or their mixtures), digestible or non-digestible carbohydrates (e.g. saccharose, maltose, fructose, glucose, dextrins, amylose, amylopectin, inulin, xylene, cellulose), sugar alcohols (e.g. sorbite), natural or hardened fats (e.g. sebum, lard, palm fat, coconut oil, hardened vegetable fat), oils (e.g. sunflower oil, peanut oil, corn oil, olive oil, fish oil, soy oil, sesame oil), fatty acid or their salts (e.g. potassium stearate), proteinogenic or non-proteinogenic amino acids and related compounds (e.g. taurine), peptides, native or processed proteins (e.g. gelatine), enzymes (e.g. peptidases), nucleic acids, nucleotides, taste correctants for unpleasant taste impressions (e.g. hesperetin, phloretin or other hydroxychalcon derivatives to be used according to US 2008/0227867 as well as optionally the lactones mentioned there), taste correctants for further, usually not unpleasant taste impressions, taste modulating substances (e.g. inositol phosphate, nucleotides such as guanosine monophosphate, adenosine monophosphate or other substances such as sodium glutamate or 2-phenoxy propionic acid), emulsifiers (e.g. lecithins, diacylglycerols), stabilizers (e.g. carrageenan, alginate), preservatives (e.g. benzoic acid, sorbic acid), antioxidants (e.g. tocopherol, ascorbic acid), chelators (e.g. citric acid), organic or inorganic acidifiers (e.g. malic acid, acetic acid, citric acid, tartatic acid, phosphoric acid, lactic acid), additional bitter substances (e.g. chinine, caffeine, limonin, amarogentin, humolone, lupolone, catechins, tannins), sweeteners (e.g. saccharin, cyclamate, aspartame, neotame, steviosides, rebaudiosides, acesulfam K, neohesperidin dihydrochalcone, thaumatin, superaspartame), mineral salts (e.g. sodium chloride, potassium chloride, magnesium chloride, sodium phosphate), substances inhibiting the enzymatic browning (e.g. sulfit, ascorbic acid), essential oils, plant extracts, natural or synthetic dyes or dye pigments (e.g. carotinoids, flavonoids, anthocyans, chlorophyll and their derivatives), spices, synthetic, natural or nature identical aromatic substances or flavours such as olfactory correctants.

A further aspect of the present invention relates to the use of an aromatic blend according to the invention as described above for imparting, modifying and/or enhancing one or more olfactory and/or gustatory scents selected from the group consisting of meat, particularly chicken, lamb or beef, fatty, rancid, nutty, sour, sweet, vegetable and fruit, preferably cucumber, melon, pear, apple, passionfruit, asparagus, tomato, and dairy, preferably sour cream, yoghurt, cheese and/or for aromatizing a composition, preferably a composition serving for food or pleasure, or a semi-finished product for preparing said composition, preferably in an amount sufficient for imparting, modifying and/or enhancing one or more olfactory and/or gustatory scents selected from the group consisting of meat, particularly chicken, lamb or beef, fatty, rancid, nutty, sour, sweet, vegetable and fruit, preferably cucumber, melon, pear, apple, passionfruit, asparagus, tomato, and dairy, preferably sour cream, yoghurt, cheese.

The embodiments of the method according to the invention described herein correspond to or can be derived from previously described embodiments of the aromatic blends, compositions and uses according to the invention and vice-versa. The embodiments described herein may furthermore, as far as technically reasonable for a skilled person, be arbitrarily combined with each other.

The present invention is subsequently further explained by the means of examples. The percentage indications indicated in the examples are relative percentages which were determined via gas chromatography. A correction factor of triacetin was not used.

Production of the Aromatic Blends

Example 1

Reaction of Pomegranate Seed Oil 10 g pomegranate seed oil are treated with air (20 L/h) at 120° C. for 6 h. Subsequently, the reaction mixture is heated to 170° C. for 1 h. Subsequently, 8.5 g of this raw material are mixed with 0.8 g triacetin and the desired product is subsequently distilled together with the triacetin (conditions: 0.5 mbar, 180° C., 1 h).

After distillative purification, the obtained solution (0.83 g) contains 96.04% triacetin, 0.22% 2E,4Z-nonadienal as well as 0.25% 2E,4E-nonadienal.

Evaluation (smell): lamb meat, fatty, rancid.

Example 2

Reaction of Pomegranate Seed Oil 11 g of pomegranate seed oil are treated with air (20 L/h) at 50° C. for 6 h. Subsequently, the reaction mixture is heated to 170° C. for 1 h. Subsequently, 10 g of this raw material are mixed with 1.0 g triacetin and the desired product is subsequently distilled together with the triacetin (conditions: 0.5 mbar, 180° C., 1 h).

After distillative purification, the obtained solution (1.01 g) contains 96.50% triacetin, 0.22% 2E,4Z-nonadienal as well as 0.07% 2E,4E-nonadienal.

Evaluation (smell): fatty, sour, sweet, lamb meat.

Example 3

Reaction of Pomegranate Seed Oil 11 g of pomegranate seed oil are treated with air (20 L/h) at 170° C. for 6 h. Subsequently, 10 g of this raw material are mixed with 1.0 g triacetin and the desired product is subsequently distilled together with the triacetin (conditions: 0.5 mbar, 180° C., 1 h).

After distillative purification, the obtained solution (1.03 g) contains 96.50% triacetin, 0.12% 2E,4Z-nonadienal as well as 0.27% 2E,4E-nonadienal.

Evaluation (smell): lamb meat, fatty, rancid.

Example 4

Reaction of Pomegranate Seed Oil 10 g of pomegranate seed oil are treated with air (20 L/h) at 170° C. for 6 h. Subsequently, the reaction mixture is heated to 170° C. for 1 h. Subsequently, 9.5 g of this raw material are mixed with 0.9 g triacetin and the desired product is subsequently fractionated distilled together with the triacetin at the (Kugelrohr) ball tube distillery (conditions: 0.5 mbar, 180° C., 1 h).

Fraction 1 (0.5 mbar, 90° C., 0.5 h) contains 98.22% triacetin, 0.04% 2E,4Z-nonadienal as well as 0.03% 2E,4E-nonadienal.

Evaluation of smell (fraction 1): sour, olive scent, fruity, slightly green.

Fraction 2 (0.5 mbar, 130° C., 0.5 h) contains 96.55% triacetin, 0.42% 2E,4Z-nonadienal as well as 0.50% 2E,4E-nonadienal.

Evaluation of smell (fraction 2): fatty, lamb, slightly rancid.

Fraction 3 (0.5 mbar, 160° C., 0.5 h) contains 92.93% triacetin, 0.30% 2E,4Z-nonadienal as well as 0.51% 2E,4E-nonadienal.

Evaluation of smell (fraction 3): lamb meat, fatty, slightly nutty.

This example shows that by separating the more slightly volatile components via a fractionated distillation, the sensorial value of these compounds is clearly increased.

Example 5

Reaction of Sunflower Oil 1.0 kg of sunflower oil are treated with air (32 L/h) at 120° C. for 6 h. Subsequently, the reaction mixture is heated to 150° C. for 2 h as well as subsequently for 0.5 h to 170° C. Subsequently, this approach is mixed with 56.0 g triacetin and the desired product is subsequently distilled together with the triacetin (conditions: 0.2 mbar, inner temperature: 175° C.).

After distillative purification, the obtained solution (34.8 g) contains 87.7% triacetin, 4.26% 2E,4Z-decadienal as well as 0.88% 2E,4E-decadienal.

Application of the previously obtained aromatic blends in semi-finished products or, respectively, compositions Application Example 1

Chicken Flavour

| Component | (g) |
| --- | --- |
| Acetylmethyl carbinol | 0.20 |
| Butyric acid | 2.00 |
| Capronic acid | 1.00 |
| Caprylic acid | 1.00 |

-continued

| Component | (g) |
|---|---|
| 2,4-Decadienal (Example 5) | 16.00 |
| Decenal-tr.2 | 0.20 |
| Dimethyloxyfuron/Sotolon (1% solution) | 0.40 |
| Furaneol (10% solution) | 20.00 |
| Indol (1% solution) | 0.40 |
| 2,3-Methylfuranthiol | 0.80 |
| Methyltetrahydrofuranthiol | 0.30 |
| Methylthiopropanal-3 | 0.15 |
| 2,4-Nonadienal (analogous example 4, fraction 2) | 30.00 |
| Thiobutanone-3,2 | 1.00 |
| Vegetable oil triglycerides | 926.55 |
| Sum | 1000.00 |

This aromatic blend is used in the subsequently described application examples.

Application Example 2

Spray Dried Aroma Composition

A spray dried aroma composition is—starting from the previously described application example 1—prepared, which is subsequently further used:

| Ingredient | A |
|---|---|
| Capsule | 200 g |
| Maltodextrin | 600 g |
| Aroma composition application example 1 | 200 g |
| Water | 1000 g |

The ingredients are dissolved in demineralized water and subsequently spray dried. These are used in the subsequent application examples.

Application Example 3

Instant Soup, Type Chicken Soup with Noodles

A=composition for comparison
B=composition according to the invention

| Ingredient | A | B |
|---|---|---|
| Starch | 16 g | 16 g |
| Sodium chloride | 7 g | 7 g |
| Saccharose, refined | 3.2 g | 3.2 g |
| Sodium glutamate | 3.2 g | 3.2 g |
| Sodium inosinate/sodium guanylate in a ratio of 1:1 | 0.8 g | 0.8 g |
| Acid hydrolyzed plant protein | 8.0 g | 8.0 g |
| Fat powder | 2.0 g | 2.0 g |
| Vegetable fat, spray dried | 1.0 g | 1.0 g |
| Freeze-dried chicken meat, in pieces | 2.15 g | 2.15 g |
| Soup noodles | 32.0 g | 32.0 g |
| Maltodextrin | 12.0 g | 7.6 g |
| Chinese vegetables, freeze-dried | 4.6 g | 4.6 g |
| Chicken flavour | 8.0 g | 6.9 g |
| Food dye riboflavin | 0.05 g | 0.05 g |
| Spray dried aroma composition of application example 2 | —/— | 5.5 g |

4.6 g of the powder mixture are boiled in 100 ml water for 10 minutes to obtain a ready-to-eat soup. The composition according to the invention B is evaluated with regard to desired fatty flavours reminding of chicken skin as stronger and longer-lasting as composition A, which results in a clearly more authentic profile.

Application Example 4

Bouillon

A=composition for comparison
B=composition according to the invention

| Ingredient | A | B |
|---|---|---|
| Fat powder | 8.77 g | 8.77 g |
| Sodium glutamate | 8.77 g | 8.77 g |
| Yeast extract powder | 12.28 g | 12.28 g |
| Sodium chloride | 29.83 g | 29.83 g |
| Maltodextrin | 37.28 g | 20.78 g |
| Natural vegetable extract | 3.07 g | 3.07 g |
| Spray dried aroma composition of application example 2 | —/— | 16.5 g |

15 g of the powder mixture are infused with 1000 ml of hot water. When tasted by a panel of skilled test persons, the composition according to the invention B is assessed as clearly more rich, balanced, strong and long-lasting with regard to its aroma and taste than the composition for comparison A.

Application Example 5

White Sauce

A=composition for comparison
B=composition according to the invention

| Component | A | B |
|---|---|---|
| Maltodextrin | 26.00 g | 23.25 g |
| Sodium chloride | 7.50 g | 7.50 g |
| Sodium glutamate | 2.00 g | 2.00 g |
| Vegetable fat | 5.00 g | 5.00 g |
| Pepper, white | 0.02 g | 0.02 g |
| Onion powder | 1.48 g | 1.48 g |
| Pre-gelatinized corn starch | 30.00 g | 30.00 g |
| Fat powder | 28.00 g | 28.00 g |
| Spray dried aroma composition of application example 2 | —/— | 2.75 g |

90 g of the sauce mixture are infused with 1000 ml hot water and strongly stirred with a whisk. When tasted by a panel of skilled test persons, the composition according to the invention B is assessed as clearly more rich, balanced, strong and long-lasting with regard to its aroma and taste than the composition for comparison A.

Application Example 6

Brown Sauce

A=composition for comparison
B=composition according to the invention

| Component | A | B |
|---|---|---|
| Starch | 40.00 g | 40.00 g |
| Maltodextrin | 33.10 g | 30.35 g |
| Sodium chloride | 6.00 g | 6.00 g |
| Caramel, spray dried | 5.00 g | 5.00 g |

-continued

| Component | A | B |
|---|---|---|
| Yeast extract powder | 3.00 g | 3.00 g |
| Sodium glutamate | 2.00 g | 2.00 g |
| Sugar | 0.50 g | 0.50 g |
| Fat powder | 5.00 g | 5.00 g |
| Tomato powder | 3.00 g | 3.00 g |
| Natural vegetable extract | 1.00 g | 1.00 g |
| Onion extract | 0.30 g | 0.30 g |
| Pepper extract | 0.10 g | 0.10 g |
| Dry flavour | 1.00 g | 1.00 g |
| Spray dried aroma composition of application example 2 | —/— | 2.75 g |

90 g of the sauce mixture are infused with 1000 ml hot water and strongly stirred with a whisk. When tasted by a panel of skilled test persons, the composition according to the invention B is assessed as clearly more rich, balanced, strong and long-lasting with regard to its aroma and taste than the composition for comparison A.

Application Example 7

Spice Mixture for Potato Chips

A=composition for comparison
B=composition according to the invention

| Component | A | B |
|---|---|---|
| Sodium glutamate | 3.50 g | 3.50 g |
| Cheese powder | 10.00 g | 10.00 g |
| Garlic powder | 2.00 g | 2.00 g |
| Whey powder | 38.86 g | 36.86 g |
| Spice extract oil | 0.20 g | 0.20 g |
| Bell pepper powder | 9.80 g | 9.80 g |
| Sodium chloride | 21.00 g | 19.00 g |
| Tomato powder | 9.00 g | 9.00 g |
| Dry flavour | 2.50 g | 2.50 g |
| Silicon dioxide | 0.02 g | 0.02 g |
| Vegetable oil | 0.02 g | 0.02 g |
| Onion powder | 3.00 g | 3.00 g |
| Cream flavour concentrate | 0.03 g | 0.03 g |
| Cheese flavour | 0.03 g | 0.03 g |
| Tomato flavour concentrate | 0.04 g | 0.04 g |
| Spray dried aroma composition of application example 2 | —/— | 4.00 g |

6 g of the spice mixture are applied on 94 g of potato chips.

Application Example 8

Chicken Meat Spice Mixture for (Instant) Noodles

| Ingredient | wt.-% |
|---|---|
| Chicken flavour | 5.00 |
| Caramel | 3.00 |
| Citric acid (water free) | 0.40 |
| Chive (drained) | 2.00 |
| Maltodextrin (ex Tapoica) | 5.30 |
| Mono sodium glutamate | 15.00 |
| Onion powder | 5.00 |
| Ribotide | 0.80 |
| Sodium chloride | 39.20 |
| Sugar | 2.80 |
| Sweet whey powder | 6.50 |
| Spray dried aroma composition of application example 2 | 15.00 |

All ingredients are mixed until a homogeneous mixture is obtained.

Application Example 9

Pear Flavour

| Ingredient | (g) |
|---|---|
| Aldehyde C6 (Hexanal) | 0.20 |
| Alcohol C6 (Hexanol) | 1.00 |
| 2,4-nonadienal (Example 2) | 0.30 |
| 2,4-decadienal (Example 5) | 0.02 |
| Butyl acetate | 30.00 |
| Ethyl butyrate | 2.00 |
| Ethyl decadienoat tr., cis 2,4 | 4.00 |
| Hexenyl acetate, cis 3 | 1.00 |
| Hexenyl acetate, trans 2 | 2.00 |
| Hexyl acetate | 35.00 |
| Propylene glycol | 924.48 |
| Sum | 1000.00 |

Typically, 10 g of the flavour described herein are used per 100 L instant drink.

Application Example 10

Passionfruit Flavour

| Ingredient | (g) |
|---|---|
| Nonalactone, gamma | 3.00 |
| Decalactone, gamma | 13.00 |
| Decadienal-2,4 tr.tr. (0.1% solution) | 0.08 |
| Ethyl butyrate | 13.00 |
| Ethyl capronate | 13.00 |
| Furfural | 12.00 |
| Geraniol | 0.30 |
| Ionon, beta | 3.00 |
| Isovaleraldehyde | 0.20 |
| 2,4-Nonadienal (Example 1) | 1.20 |
| Thiomentanone-8,3 | 0.13 |
| Phenylethylalcohol | 6.50 |
| Terpineol alpha | 10.00 |
| Propylene glycol | 924.59 |
| Sum | 1000.00 |

Typically, 10 g of the flavour described herein are used per 100 L instant drink.

Application Example 11

Mushroom Flavour

| Ingredient | (g) |
|---|---|
| Octanol-1 | 4.00 |
| Caprylic acid | 15.00 |
| 2,4-Decadienal (Example 5) | 60.00 |

| Ingredient | (g) |
| --- | --- |
| Decalactone, delta | 7.00 |
| 2,4-Nonadienal (example 4, fraction 2) | 200.00 |
| Octenol-1,3 | 50.00 |
| Octenone-1,3 | 3.00 |
| Triacetin | 661.00 |
| Sum | 1000.00 |

Typically, 10 g of the flavour described herein are needed per 100 kg soup.

The invention claimed is:

1. A method for producing one or more unsaturated dienals, the method comprising:
   (a) subjecting an oil comprising punicic acid, punicic acid ester, elaeostearinic acid, elaeostearinic acid ester, linoleic acid, linoleic acid ester, or a combination thereof to air oxidation at a temperature of 70 to 200° C. and forming a mixture comprising:
      (i) dienals selected from 2,4-nonadienal, 2,4-decadienal, and a combination thereof; and
      (ii) residual oil; and
   (b) separating dienals from the mixture of (a) to obtain purified or concentrated dienals selected from 2,4-nonadienal, 2,4-decadienal, and a combination thereof, and a residue separate from the purified or concentrated dienals.

2. The method of claim 1, wherein the residue of (b) is reused in (a).

3. The method of claim 1, wherein the oil of (a) is mixed with one or more solvents to form an oil and solvent mixture that is subjected to the air oxidation.

4. The method of claim 1, wherein the air oxidation of (a) is carried out by subjecting the oil to 10 to 1,000 l/h of air per kg of the oil.

5. The method of claim 1, wherein the air oxidation of (a) is carried out at a temperature of 100 to 130° C.

6. The method of claim 1, wherein the air oxidation of (a) is carried out for 1 to 30 hours.

7. The method of claim 1, further comprising heating the mixture of (a) formed by the air oxidation.

8. The method of claim 1, wherein the dienals are separated in (b) by distillation.

9. The method of claim 1, wherein one or more solvents are added to the mixture of (a) before separating the dienals from the mixture in (b).

10. The method of claim 1, further comprising washing the mixture of (a) with an aqueous alkaline solution before separating the dienals from the mixture in (b).

11. The method of claim 3, wherein the one or more solvents are selected from triacetin, triethyl citrate, and a combination thereof.

12. The method of claim 3, wherein the oil and solvent mixture comprises 2 to 20 wt. % of the one or more solvents, based on the total weight of the oil.

13. The method of claim 6, wherein the air oxidation of (a) is carried out for 4 to 12 hours.

14. The method of claim 7, wherein the mixture of (a) is heated to a temperature of 100 to 200° C. for 0.5 to 5 hours.

* * * * *